(12) United States Patent
Dang et al.

(10) Patent No.: US 9,120,994 B2
(45) Date of Patent: Sep. 1, 2015

(54) TERPENE ALCOHOLS FOR USE IN FRAGRANCE COMPOSITIONS AND PERFUMED PRODUCTS

(75) Inventors: Hai-Shan Dang, Shanghai (CN); Andreas Goeke, Winterthur (CH); Yue Zou, Shanghai (CN)

(73) Assignee: Givaudan S.A., Vernier (CH)

( * ) Notice: Subject to any disclaimer, the term of this patent is extended or adjusted under 35 U.S.C. 154(b) by 94 days.

(21) Appl. No.: 14/117,983

(22) PCT Filed: May 25, 2012

(86) PCT No.: PCT/EP2012/059815
§ 371 (c)(1),
(2), (4) Date: Mar. 14, 2014

(87) PCT Pub. No.: WO2012/160189
PCT Pub. Date: Nov. 29, 2012

(65) Prior Publication Data
US 2015/0038386 A1    Feb. 5, 2015

(30) Foreign Application Priority Data

May 25, 2011    (WO) ................ PCT/CN2011/000894

(51) Int. Cl.
| | | |
|---|---|---|
| A61K 8/00 | (2006.01) | |
| C11B 9/00 | (2006.01) | |
| C07C 33/02 | (2006.01) | |
| C07C 33/05 | (2006.01) | |
| A61K 8/34 | (2006.01) | |
| A61Q 5/02 | (2006.01) | |
| A61Q 19/10 | (2006.01) | |
| C11D 3/50 | (2006.01) | |

(52) U.S. Cl.
CPC . *C11B 9/003* (2013.01); *A61K 8/34* (2013.01); *A61Q 5/02* (2013.01); *A61Q 19/10* (2013.01); *C07C 33/02* (2013.01); *C07C 33/05* (2013.01); *C11B 9/0015* (2013.01); *C11D 3/50* (2013.01); *A61K 2800/10* (2013.01); *C07C 2101/02* (2013.01)

(58) Field of Classification Search
CPC ................................ C07C 33/02; C07C 33/05
USPC ...................................................... 512/8, 27
See application file for complete search history.

(56) References Cited

U.S. PATENT DOCUMENTS

| | | | |
|---|---|---|---|
| 4,604,488 A | 8/1986 | Fujikura et al. | |
| 2007/0238629 A1 | 10/2007 | Kane et al. | |
| 2009/0016976 A1 | 1/2009 | Turin | |
| 2010/0069508 A1 | 3/2010 | Bajgrowicz | |

FOREIGN PATENT DOCUMENTS

| | | |
|---|---|---|
| FR | 2 539 624 | 7/1984 |
| GB | 1 278 178 | 6/1972 |
| JP | 48032811 A | 5/1973 |
| WO | WO 2006/069224 A2 | 6/2006 |
| WO | WO 2007/130218 A1 | 11/2007 |
| WO | WO 2008/052379 A2 | 5/2008 |

OTHER PUBLICATIONS

Sun Li-hong et al., "Progress on Study of Geraniol", Northwest Pharmaceutical Journal, Oct. 2009, China Academic Journal Electronic Publishing House, pp. 428-430, vol. 24, No. 5.
Ran Xue-guang, et al., "Progress on Synthesis of Citronellol", Chemistry and Industry of Forest Products, Sep. 2003, China Academic Journal Electronic Publishing House, pp. 97-101, vol. 23, Issue 3. (English Abstract only).
PCT/EP2012/059815—International Search Report, Oct. 30, 2012.
PCT/EP2012/059815—International Written Opinion, Oct. 30, 2012.
PCT/EP2012/059815—International Preliminary Report on Patentability, Nov. 26, 2013.
PCT/CN2011/000894—International Search Report, Mar. 15, 2012.
PCT/CN2011/000894—International Written Opinion, Mar. 15, 2012.
PCT/CN2011/000894—International Preliminary Report on Patentability, Nov. 26, 2013.
Surburg, et al., "Common Fragrance and Flavor Materials" Preparation, Properties and Uses, 5Completely Revised and Enlarged edition, Jan. 1, 2006, pp. 27-38.
European Office Action for corresponding European Application Patent No. EP 12 726 769.8-1454, issued on Oct. 24, 2014.

*Primary Examiner* — John Hardee
(74) *Attorney, Agent, or Firm* — Curatolo Sidoti Co., LPA; Joseph G. Curatolo; Salvatore A. Sidoti

(57) ABSTRACT

Compounds of formula (I)

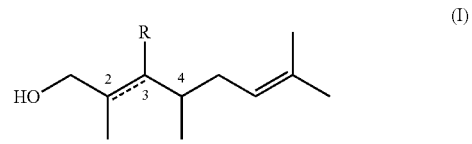

wherein R is hydrogen and the bond between C-2 and C-3 together with the dotted line represents a double bond, or R is —CH$_2$— and together with C-2 and C-3 represents a cyclopropane ring and the bond between C-2 and C-3 together with the dotted line represents a single bond, having floral rosy odor notes, their use as fragrance and perfumed products comprising them.

10 Claims, No Drawings

TERPENE ALCOHOLS FOR USE IN FRAGRANCE COMPOSITIONS AND PERFUMED PRODUCTS

CROSS REFERENCE TO RELATED APPLICATIONS

This application is a national stage application of International Application No. PCT/EP2012/059815, filed 25 May 2012, which claims priority from International Application No. PCT/CN2011/000894, filed 25 May 2011, from which applications priority is claimed, and which are incorporated herein by reference.

The present invention relates to trimethyloctadienol and derivatives thereof having floral rosy odor notes. This invention relates furthermore to their use as fragrance ingredient and to fragrance compositions and perfumed products comprising them. It furthermore relates to a method of their production.

Floral rosy odor characteristics are an important scent in perfumery. Albeit a wide range of compounds possessing floral and rosy odor notes are known there is a constant demand for new compounds that enhance, modify or improve on odor notes.

According to our best knowledge, none of the inventions' compounds have been described in the prior art. The closest analogues with a similar structure, one may cite 3,7-dimethyloct-6-enol (citronellol) and 3,7-dimethyloct-2,6-dienol (Geraniol). However, said compounds have a substitution pattern substantially different, not to mention the fact that the odor strengs (which may be expressed by the odor threshold concentration) and diffusivity (which may be measured by the odor value, i.e. the ratio of the vapor pressure and its mean odor threshold concentration) are totally different.

It has now been found that 2,4,7-trimethylocta-2,6-dien-1-ol and derivatives thereof constitute a new, well defined class of odorants possessing surprisingly low odor threshold concentrations compared to compounds with similar structures and exhibiting desirable floral rosy odor characteristics making them particularly suitable for use as fragrance ingredients. Because of their low odor threshold concentration, it is possible to use much lower concentrations of the compounds of the present invention compared to 3,7-dimethyloct-6-enol or 3,7-dimethyloct-2,6-dienol to achieve an olfactory effect.

Accordingly, in a first aspect there is provided the use as fragrance of a compound of formula (I)

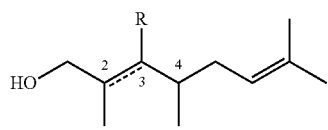

(I)

wherein
R is hydrogen and the bond between C-2 and C-3 together with the dotted line represents a double bond; or
R is —CH$_2$— and forms together with C-2 and C-3 a cyclopropane ring and the bond between C-2 and C-3 represents together with the dotted line a single bond.

As a typical example one may cite (E/Z)-2,4,7-trimethylocta-2,6-dien-1-ol possessing a rosy but more geranium citrus-like note.

As a further example one may cite [1-methyl-2(5-methylhex-4-en-2-yl)cyclopropyl]methanol possessing a floral rosy, geranium-like, diffusive odor note. Said compound comprises three stereogenic centres and thus may exist as a mixture of up to eight stereoisomers, or in its diastereomerically pure or even enantiomerically pure forms. Some of the individual isomers have different odor qualities, both in terms of performance as well as olfactory properties.

For example one may cite [(1S*,2R*)-1-methyl-2-[(R*)-5-methylhex-4-en-2-yl]cyclopropyl]methanol (Ic) possessing in addition to its overall floral rosy odor notes a citrus and phenoxanol-like note. [(1S*,2R*)-1-methyl-2-[(R*)-5-methylhex-4-en-2-yl]cyclopropyl]methanol has an extremely low odor threshold concentration which is, for example, 100 times lower than [(1S*,2R*)-1-methyl-2-[(S*)-5-methylhex-4-en-2-yl]cyclopropyl]methanol (Ib) and is therefore of particular interest.

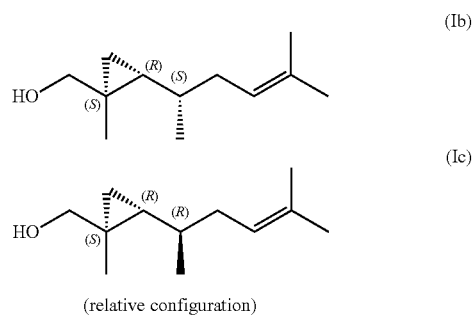

(relative configuration)

The compounds of formula (I) may be used alone, as mixtures thereof, and/or in combination with a base material. As used herein, the "base material" includes all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

In one embodiment the compounds of formula (I) are used as a mixture of 2,4,7-trimethylocta-2,6-dien-1-ol (Ia), [(1S*,2R*)-1-methyl-2-[(S*)-5-methylhex-4-en-2-yl]cyclopropyl] methanol (Ib) and [(1S*,2R*)-1-methyl-2-[(R*)-5-methylhex-4-en-2-yl]cyclopropyl]methanol (Ic) wherein the mixtures comprises up to 20% by weight of (Ia), e.g., 1 to 15% by weight (including 5, 7, 10, 12% by weight).

In an other embodiment the compounds of formula (I) are used as a mixture of 2,4,7-trimethylocta-2,6-dien-1-ol (Ia), [(1S*,2R*)-1-methyl-2-[(S*)-5-methylhex-4-en-2-yl]cyclopropyl]methanol (Ib) and [(1S*,2R*)-1-methyl-2-[(R*)-5-methylhex-4-en-2-yl]cyclopropyl]methanol (Ic) wherein the mixtures comprises up to 20% by weight of (Ia), e.g., about 1 to about 15% by weight (including 5, 7, 10, 12% by weight), and at least 10% by weight of (Ic), e.g. about 10 to 80% by weight (including 15, 20, 25, 30, 35, 40, 45. 50, 55, 60, 65, 70, 75% by weight).

As used herein, "fragrance composition" means any composition comprising at least one compound of formula (I) and a base material, e.g. a diluent conventionally used in conjunction with odorants, such as dipropyleneglycol (DPG), isopropylmyristate (IPM), triethylcitrate (TEC) and alcohol (e.g. ethanol), and known odorants.

The following list comprises examples of known odorant molecules, which may be combined with the compounds of the present invention:

essential oils and extracts, e.g. tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol™, eugenol, farnesol, geraniol, Super Muguet™, linalool, menthol, nerol, phenylethyl alcohol, rhodinol, Sandalore™, terpineol or Timberol™;

aldehydes and ketones, e.g. anisaldehyde, α-amylcinnamaldehyde, Georgywood™, hydroxycitronellal, Iso E® Super, Isoraldeine®, Hedione®, Lilial®, maltol, Methyl cedryl ketone, methylionone, verbenone or vanillin;

ethers and acetals, e.g. Ambrox™, geranyl methyl ether, rose oxide or Spirambrene™;

esters and lactones, e.g. benzyl acetate, Cedryl acetate, γ-decalactone, Helvetolide®, δ-undecalactone or Vetivenyl acetate;

macrocycles, e.g. Ambrettolide, Ethylene brassylate or Exaltolide®;

heterocycles, e.g. isobutylquinoline.

The compounds according to formula (I) may be used in a broad range of perfumed products, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients. The proportion is typically from 0.0001 to 30 weight percent of the application. In one embodiment, compounds of the present invention may be employed in a fabric softener in an amount of from 0.001 to 50 weight percent. In another embodiment, compounds of the present invention may be used in fine perfumery in amounts of from 0.01 to 30 weight percent, more preferably between 0.5 and 20 weight percent. However, these values are given only by way of example, since the experienced perfumer may also achieve effects or may create novel accords with lower or higher concentrations, e.g. up to about 50 weight percent based on the perfumed product.

The compounds as described hereinabove may be employed in a consumer product base simply by directly mixing at least one compound of formula (I), or a fragrance composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base.

Thus, the invention additionally provides a method of manufacturing a perfumed product, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactorily acceptable amount of at least one compound of the present invention as hereinabove described the odor notes of a consumer product base will be improved, enhanced or modified.

Thus, the invention furthermore provides a method for improving, enhancing or modifying a consumer product base by means of the addition thereto of an olfactorily acceptable amount of at least one compound of formula (I).

The invention also provides a perfumed product comprising:
a) as odorant at least one compound of formula (I); and
b) a consumer product base.

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body-care products, e.g. shampoo, shower gel; air care products and cosmetics, e.g. deodorant, vanishing cream. This list of products is given by way of illustration and is not to be regarded as being in any way limiting.

To the best of our knowledge none of the compounds falling within the definition of formula (I) are described in the literature and are thus novel in their own right.

Accordingly, the present invention refers in a further aspect to compounds of formula (I)
wherein

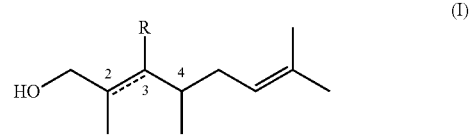

R is hydrogen and the bond between C-2 and C-3 together with the dotted line represents a double bond; or
R is —CH$_2$— and together with C-2 and C-3 represents a cyclopropane ring and the bond between C-2 and C-3 together with the dotted line represents a single bond.

Particularly preferred are compounds wherein the substituents at C-2 and C-3 in trans-position to each other.

Compounds of formula (I) may be prepared by art recognized methods under conditions known to the skilled person. Further particulars referring to reaction conditions are provided in the examples.

The invention is now further described with reference to the following non-limiting examples. These examples are for the purpose of illustration only and it is understood that variations and modifications can be made by one skilled in the art.

EXAMPLE 1

2,4,7-Trimethylocta-2,6-dien-1-ol

A) The amine-H$_4$PO$_3$ catalyst (2.0 g, 1 w/w %) prepared by mixing orthophosphoric acid (85%) with triethanolamine (in 1:1 equivalent) was dissolved in acetic acid (4 ml, 2 ml/w %) and added to a mixture of 1,1-dimethoxy-2-methylpent-2-ene (200 g, 1.52 mol) and 3-methyl-but-2-en-1-ol (131 g, 1.52 mol). The mixture was heated to 110° C. for 2 h, then at 160° C. for further 4 h. During this period, volatile materials were collected through a 10 cm Vigreux column. The remaining oil was distilled in vacuo to give 2,4,7-trimethylocta-2,6-dienal (66%).

B) To a suspension of LiAlH$_4$ (4.8 g, 126 mmol) in THF (100 ml) was added dropwise a solution of 2,4,7-trimethylocta-2,6-dienal (20 g, 114 mmol) in THF (60 ml) at 5° C. over 1 h. The mixture was stirred at room temperature for 1 h.

5 ml of water, 5 ml of 15% aq. NaOH and 15 ml of water were carefully added subsequently. The mixture was stirred for 1 h. Precipitates were filtered and the filtrate was concentrated in vacuo. The residue was Kugelrohr-distilled to give 2,4,7-trimethylocta-2,6-dien-1-ol (98%). bp: 82-83° C./1 mbar.

$^1$H-NMR (300 MHz, CDCl$_3$): 5.22 (d, 1H, J=9.4, Hz, H-3), 5.09 (t, 1H, J=7.2 Hz, H-6), 3.99 (brs, 2H, H-1), 2.48-2.33 (m, 1H, H-4), 2.05-1.90 (m, 2H, H-5), 1.69 (s, 3H, 2-Me), 1.66 (s, 3H, 7-Me), 1.59 (s, 3H, 7-Me'), 0.95 (d, 3H, J=6.3 Hz, 4-Me) ppm. $^{13}$C-NMR (75 MHz, CDCl$_3$): 133.2 (s, C-2), 132.5 (d, C-3), 132.2 (5, C-7), 122.8 (d, C-6), 69.1 (t, CH$_2$OH), 35.6 (t, C-5), 32.7 (d, C-4), 25.8 (q, 7-Me), 20.4 (q, 4-CH$_3$), 17.8 (q, 7-Me'), 13.8 (q, 2-Me) ppm. GC/MS (EI), two isomers in a ratio of 17:1, major E-isomer: 168 (M$^+$, 1), 150 (1), 137 (2), 99 (20), 82 (7), 69 (24), 55 (9), 43 (100).

Odor description: floral, rose and geranium-like with citrus note.

EXAMPLE 2

[1-Methyl-2(5-methylhex-4-en-2yl)cyclopropyl]methanol

To a mixture 2,4,7-trimethylocta-2,6-dien-1-ol (20 g, 119 mmol) and lithium granules (1.7 g, 240 mmol) in THF (50 ml) was added dropwise sec-chlorobutane (11 g, 120 mmol) in THF (40 ml) at 10-15° C. over 0.5 h. The resulting deep grey solution was stirred for further 0.5 h at 15° C. Dibromomethane (59 g, 340 mmol) and tert-butylmagnesium (340 mmol, 1.7 M in THF) were added separately at the same time over 2 h at 10° C. The resulting mixture was stirred for further 1 h, and then poured into cold 3 N aqueous HCl solution (200 ml). The organic phase was separated. The aqueous phase was extracted with MTBE (3×20 ml). The combined organic phase was washed with 20 ml of sat. NaHCO$_3$, dried. The solvent was removed. The residue was distilled in vacuo through a short Vigreux column to give a mixture of (E)-2,4,7-trimethylocta-2,6-dien-1-ol (one main isomer) and (1-methyl-2(5-methylhex-4-en-2yl)cyclopropyl)methanol (I) (2 main isomers) in a ratio of 1 (Ia):4.6 (Ib):2.6 (Ic) in a yield of 92%. Boiling point: 80-85° C./0.15 mbar.

$^1$H-NMR (300 MHz, CDCl$_3$): 5.18-5.01 (m, 1H, Me$_2$C=CHCH$_2$), 3.32-3.17 (m, 2H, CH$_2$OH), 2.14-1.82 (m, 2H, =CHCH$_2$), 1.65, 1.63 (2s, 3H, MeCH$_3$C=CH), 1.55, 1.53 (2s, 3H, MeCH$_3$C=CH), 1.09 (s, 3H, CCH$_3$), 1.06-0.95 (m, 1H, CHMe), 0.92, 0.88 (2d, 3H, J=6.1 Hz, CHCH$_3$), 0.51-0.29 (m, 2H, CHCH and cyclopropane-methylene H$^A$), 0.02-0.11 (m, 1H, cyclopropane-methylene H$^B$) ppm. $^{13}$C-NMR (75 MHz, CDCl$_3$) two major isomers: 132.4, 131.9, (2s, Me$_2$C=CH), 123.3, 123.0, (2d, Me$_2$C=CH), 72.5, 68.9 (2t, CH$_2$OH), 36.0, 35.5 (2t, Me$_2$C=CHCH$_2$), 34.6, 33.7 (2d, CHMe), 29.2, 29.0 (2d, cyclopropanated-CH), 25.8, 25.7 (2q, MeCH$_3$C=CH), 23.2, 22.2 (2s, cyclopropanated-C), 20.3, 20.2 (2q, CHCH$_3$), 17.7 (3), 17.7 (1) (2q, MeCH$_3$C=CH), 16.3, 15.5 (2t, cyclopropanated-CH$_2$), 15.8, 15.3 (2q, 1-CH$_3$) ppm.

Odor description (isomer mixture): floral rosy, geranium-like, diffusive.

The isomer mixture was subjected to silica-gel flash chromatography using a 52 cm×8.5 cm column with gradient solvent (hexane-ethyl acetate) eluant.

a) [(1S*,2R*)-1-Methyl-2-[(R*)-5-methylhex-4-en-2-yl]cyclopropyl]methanol (Ic) was isolated in purity of 92.7% (GCMS) with the following data:

$^1$H-NMR (500 MHz, DMSO): 5.18-5.12 (m, 1H, Me$_2$C=CHCH$_2$), 4.36 (t, 1H, J=5.7 Hz, OH), 3.10 (d, 2H, J=5.7 Hz, CH$_2$OH), 2.09-2.02 (m, 1H, CH$_2$), 1.93-1.85 (m, 1H, CH$_2^B$), 1.65 (s, 3H, MeCH$_3$C=CH), 1.56 (s, 3H, MeCH$_3$C=CH), 1.03 (s, 3H, CCH$_3$), 1.02-0.97 (m, 1H, CHMe), 0.86 (d, 3H, J=6.7 Hz, 2-Me), 0.42 (dd, 1H, J=8.6, 4.0 Hz, cyclopropane-methylene H$^A$), 0.40-0.34 (m, 1H, cyclopropanated-CH), −0.10 (dd, 1H, J=5.1, 4.0 Hz, cyclopropane-methylene H$^B$) ppm. $^{13}$C-NMR (125 MHz, DMSO): 131.1 (s, Me$_2$C=CH), 123.1 (d, Me$_2$C=CH), 69.7 (t, CH$_2$OH), 35.3 (t, Me$_2$C=CHCH$_2$), 34.2 (d, CHMe), 27.8 (d, cyclopropanated-CH), 25.7 (q, MeCH$_3$C=CH), 21.7 (s, cyclopropanated-C), 20.1 (q, CHCH$_3$), 17.7 (q, MeCH$_3$C=CH), 15.9 (t, cyclopropanated-CH$_2$), 15.5 (q, 1-CH$_3$) ppm.

GC/MS (EI), 182 (M$^+$, <1), 164 (7), 149 (7), 139 (12), 121 (28), 109 (10), 95 (60), 81 (18), 69 (57), 55 (100), 43 (55).

Odor description: floral, rosy, phenoxanol-like, citrus.

b) [(1S*,2R*)-1-Methyl-2-[(S*)-5-methylhex-4-en-2-yl]cyclopropyl]methanol (Ib) was isolated in purity of 88.7% (GCMS) with the following data:

$^1$H-NMR (500 MHz, DMSO): 5.17-5.12 (m, 1H, Me$_2$C=CHCH$_2$), 4.37 (t, 1H, J=5.5 Hz, OH), 3.14 (dd, 1H, J=10.8, 5.5 Hz, CH$_2^A$OH), 3.05 (dd, 1H, J=10.8, 5.5 Hz, CH$_2^B$OH), 2.02-1.95 (m, 1H, CH$_2^A$), 1.94-1.82 (m, 1H, CH$_2^B$), 1.65 (s, 3H, MeCH$_3$C=CH), 1.55 (s, 3H, MeCH$_3$C=CH), 1.06-0.98 (m, 1H, CHMe), 1.02 (s, 3H, CCH$_3$), 0.90 (d, 3H, J=6.6 Hz, 2-Me), 0.42 (dd, 1H, J=9.0, 3.6 Hz, cyclopropane-methylene H$^A$), 0.37 (m, 1H, cyclopropane-CH), −0.17 (dd, 1H, J=5.0, 3.6 Hz, cyclopropane-methylene H$^B$) ppm. $^{13}$C-NMR (125 MHz, DMSO): 130.9 (s, Me$_2$C=CH), 123.1 (d, Me$_2$C=CH), 69.5 (t, CH$_2$OH), 35.5 (t, Me$_2$C=CHCH$_2$), 33.8 (d, CHMe), 28.0 (d, cyclopropanated-CH), 25.7 (q, MeCH$_3$C=CH), 21.5 (s, cyclopropanated-C), 20.2 (q, CHCH$_3$), 17.6 (q, MeCH$_3$C=CH), 16.0 (q, CCH$_3$), 15.2 (t, cyclopropanated-CH$_2$) ppm. GC/MS (EI), 182 (M$^+$, <1), 164 (7), 149 (5), 139 (7), 121 (19), 109 (13), 95 (87), 81 (18), 69 (65), 55 (100), 41 (53).

Odor description: floral, rosy, geraniol-like.

EXAMPLE 3

GC-Odor Threshold Concentration

Definition: The odour threshold concentration is defined as the lowest concentration of the vapour of an odourant material in the air which can be detected by smell and can be measured by standard methods known in the art.

According to standard procedures known to the person skilled in the art, threshold concentrations for volatile perfumery compounds are determined on a gas chromatograph equipped with a sniff port by a panel of trained evaluators. The lowest concentration smelled by each panelist is recorded as the individual threshold concentration expressed in ng (absolute amount of compound delivered at the sniff port).

Under identical conditions the odor threshold concentration for

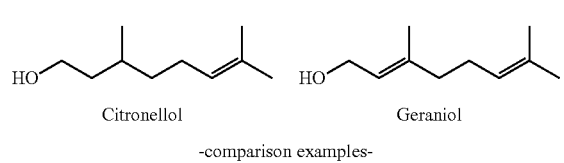

-comparison examples-

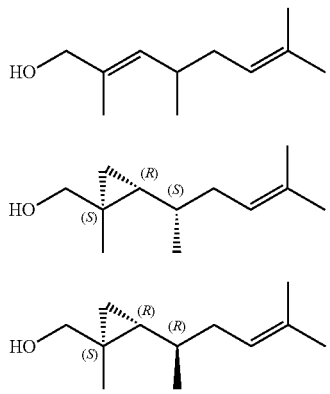

-relative configuration shown-

| Compound | Odor threshold concentration (relative) |
|---|---|
| Citronellol | 185 |
| Geraniol (cis/trans mixture) | 780 |
| Compound Ia (cis/trans 1:17) | 70 |
| Compound Ib | 100 |
| Compound Ic | 1 |

As can be seen from the results above, for example, the odor threshold concentration of compound Ia is more than 11 times lower than the odor threshold concentration of geraniol and more than 2 times lower than citronellol.

EXAMPLE 4

A Fresh Rosy Perfume for Consumer Product Applications

| Compound | parts per weight 1/940 |
|---|---|
| Benzyl acetate | 125 |
| (Dimethyl benzyl carbinyl) acetate | 12 |
| Cis hex-3-en-1-yl acetateat @ 10% in DPG | 10 |
| AGRUMEX (2-(1,1-dimethylethyl)-cyclohexanol acetate) | 10 |
| 2-phenylethanol | 200 |
| nonanal @ 50% in TEC | 3 |
| Guaiac wood oil | 4 |
| (1-methyl-2(5-methylhex-4-en-2yl)cyclopropyl)methanol (Example 2) | 10 |
| Alpha damascone @ 10% in DPG | 20 |
| Delta damascone | 2 |
| Diphenyloxide | 120 |
| DPG (Dipropylene glycole) | 100 |
| Eugenol | 4 |
| GALAXOLIDE (4,6,6,7,8,8-hexamethyl-1,3,4,6,7,8-hexahydrocyclopenta[g]isochromene) | 60 |
| Geraniol | 20 |
| Beta Ionone | 10 |
| JASMACYCLENE (3a,4,5,6,7,7a-hexahydro-4,7-Methano-1H-inden-6-ol acetate) | 125 |
| Diethyl malonate | 2 |
| MYRALDENE (4-(4-methylpent-3-en-1-yl)cyclohex-3-enecarbaldehyde) @ 10% in DPG | 20 |
| PEONILE (2-cyclohexylidene-2-phenylacetonitrile) | 10 |
| Phenethyl 2-phenylacetate | 5 |
| ROSACETOL (2,2,2-trichloro-1-phenylethyl acetate) | 10 |
| Roseoxide @ 10% in DPG | 20 |

| Compound | parts per weight 1/940 |
|---|---|
| Terpineol pure | 10 |
| 3,7-dimethyl 3-octanol | 25 |
| TRICYCLAL (2,4-dimethylcyclohex-3-enecarbaldehyde) | 3 |
| TOTAL: | 940 |

In this accord, the addition of (1-methyl-2(5-methylhex-4-en-2yl)cyclopropyl)methanol (Example 2) boosts the floral, rosy character of the detergent powder perfume, in particular in the wet and fresh rinsed phase of the washing process. It delivers a very natural rose petal like impression much appreciated in consumer product applications.

The invention claimed is:

1. A compound of formula (I)

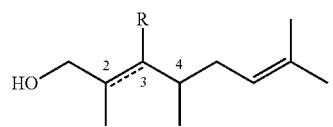

wherein
R is hydrogen and the bond between C-2 and C-3 together with the dotted line represents a double bond; or
R is —CH$_2$— and forms together with C-2 and C-3 a cyclopropane ring and the bond between C-2 and C-3 represents together with the dotted line a single bond.

2. The compound according to claim 1 selected from [(1S*,2R*)-1-methyl-2-[(R*)-5-methylhex-4-en-2-yl]cyclopropyl]methanol, [(1S*,2R*)-1-methyl-2-[(S*)-5-methylhex-4-en-2-yl]cyclopropyl]methanol, and (E)-2,4,7-trimethylocta-2,6-dien-1-ol.

3. A fragrance composition or a perfumed product comprising a compound of formula (I)

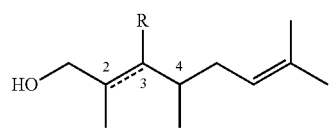

wherein
R is hydrogen and the bond between C-2 and C-3 together with the dotted line represents a double bond; or
R is —CH$_2$— and forms together with C-2 and C-3 a cyclopropane ring and the bond between C-2 and C-3 represents together with the dotted line a single bond.

4. The perfumed product according to claim 3 wherein the perfumed product is selected from fine perfumery, fabric care, household products, beauty and personal care products and air care products.

5. The fragrance composition or the perfumed product according to claim 3 wherein the compound of formula (I) is selected from [(1S*,2R*)-1-methyl-2-[(R*)-5-methylhex-4-en-2-yl]cyclopropyl]methanol, [(1S*,2R*)-1-methyl-2-[(S*)-5-methyl hex-4-en-2-yl]cyclopropyl]methanol, and (E)-2,4,7-trimethylocta-2,6-dien-1-ol.

6. The fragrance composition or the perfumed product comprising according to claim 5 comprising [(1S*,2R*)-1-methyl-2-[(R*)-5-methylhex-4-en-2-yl]cyclopropyl]methanol, and [(1S*,2R*)-1-methyl-2-[(S*)-5-methylhex-4-en-2-yl]cyclopropyl]methanol.

7. The perfumed product according to claim 6 wherein the perfumed product is selected from fine perfumery, fabric care, household products, beauty and personal care products and air care products.

8. The perfumed product according to claim 5 wherein the perfumed product is selected from fine perfumery, fabric care, household products, beauty and personal care products and air care products.

9. A method of improving, enhancing, or modifying a consumer product base comprising the step of adding thereto an olfactorily acceptable amount of at least one compound of formula (I)

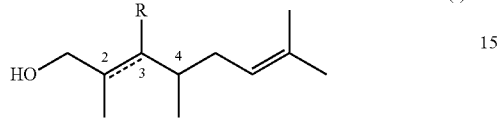

(I)

wherein
R is hydrogen and the bond between C-2 and C-3 together with the dotted line represents a double bond; or
R is —CH$_2$— and forms together with C-2 and C-3 a cyclopropane ring and the bond between C-2 and C-3 represents together with the dotted line a single bond.

10. The method according to claim 9 wherein the compound of formula (I) is selected from [(1S*,2R*)-1-methyl-2-[(R*)-5-methylhex-4-en-2-yl]cyclopropyl]methanol, [(1S*,2R*)-1-methyl-2-[(S*)-5-methylhex-4-en-2-yl]cyclopropyl]methanol, and (E)-2,4,7-trimethylocta-2,6-dien-1-ol.

* * * * *